(12) United States Patent
Sheng et al.

(10) Patent No.: US 11,331,084 B2
(45) Date of Patent: May 17, 2022

(54) PORTABLE LIQUID COLLECTION DEVICE

(71) Applicant: ZHONGSHAN HOSPITAL, FUDAN UNIVERSITY, Shanghai (CN)

(72) Inventors: Lei Sheng, Shanghai (CN); Xuening Li, Shanghai (CN); Changpeng Wang, Shanghai (CN)

(73) Assignee: ZHONGSHAN HOSPITAL, FUDAN UNIVERSITY, Shanghai (CN)

( * ) Notice: Subject to any disclaimer, the term of this patent is extended or adjusted under 35 U.S.C. 154(b) by 0 days.

(21) Appl. No.: 17/282,388

(22) PCT Filed: May 8, 2020

(86) PCT No.: PCT/CN2020/089254
§ 371 (c)(1),
(2) Date: Apr. 2, 2021

(87) PCT Pub. No.: WO2020/224651
PCT Pub. Date: Nov. 12, 2020

(65) Prior Publication Data
US 2021/0353265 A1    Nov. 18, 2021

(30) Foreign Application Priority Data
May 9, 2019    (CN) .......................... 201910384083.1

(51) Int. Cl.
*A61B 10/00*    (2006.01)
(52) U.S. Cl.
CPC ........ *A61B 10/007* (2013.01); *A61B 10/0096* (2013.01); *A61B 2560/0431* (2013.01)
(58) Field of Classification Search
None
See application file for complete search history.

(56) References Cited

U.S. PATENT DOCUMENTS

| | | | | |
|---|---|---|---|---|
| 3,137,010 A | * | 6/1964 | Ross ..................... | E03D 11/025 4/483 |
| 3,923,040 A | * | 12/1975 | Beach ................ | A61B 10/0045 600/573 |

(Continued)

FOREIGN PATENT DOCUMENTS

| CN | 102564796 A | 7/2012 |
|---|---|---|
| CN | 204346762 U | 5/2015 |

(Continued)

OTHER PUBLICATIONS

English-language machine translation of CN 108542431 A, 5 pages, printed on Oct. 21, 2021. (Year: 2021).*

*Primary Examiner* — Matthew Kremer
(74) *Attorney, Agent, or Firm* — Bayramoglu Law Offices LLC

(57) ABSTRACT

A portable liquid collection device includes a liquid collector, a guide tube and a liquid collection tube. The liquid collector includes a flowing liquid hole and an anti-slip structure. The guide tube includes two ends, one end connects to the liquid collector, and the other end is in a needle-shaped structure and connects to the liquid collection tube. A gas channel and a liquid channel are disposed in a tube body of the guide tube. The guide tube is provided with an outer annular structure. The liquid collection tube includes a collection tube body and a collection tube cover. The collection tube cover includes a tube cover body and a blocking plug. A placing slot for placing the blocking plug is disposed between the top and the bottom of the tube cover body.

16 Claims, 11 Drawing Sheets

(56) References Cited

U.S. PATENT DOCUMENTS 5,494,646 A      2/1996   Seymour
5,681,742 A * 10/1997   MersKelly .............. B01L 3/508
                                                            141/319

FOREIGN PATENT DOCUMENTS

| CN | 205333363 U | | 6/2016 | |
|----|-------------|---|--------|---|
| CN | 205941087 U | | 2/2017 | |
| CN | 206026357 U | | 3/2017 | |
| CN | 108542431 A | * | 9/2018 | |
| CN | 110169791 A | | 8/2019 | |
| GB | 2218338 A | * | 11/1989 | ........... A61B 10/007 |
| WO | 2016068816 A1 | | 5/2016 | |

* cited by examiner

PORTABLE LIQUID COLLECTION DEVICE

CROSS REFERENCE TO THE RELATED APPLICATIONS

This application is the national phase entry of International Application No. PCT/CN2020/089254, filed on May 8, 2020, which is based upon and claims priority to Chinese Patent Application No. 201910384083.1, filed on May 9, 2019, the entire contents of which are incorporated herein by reference.

TECHNICAL FIELD

The present invention relates to the technical field of liquid collection, and more particularly, to a portable liquid collection device.

BACKGROUND

With the steady improvement of living standards, people are paying more and more attention to health. The changes in current work habits, however, have people sitting for a long time and drinking less water. Long-term bad work habits have caused many urinary diseases that endanger health and well being, such as kidney stones, urinary tract infections, prostatitis, and so on. Thus, laboratory examinations such as urine routine, urine sediment are also increasing year by year in conventional diagnosis and treatment.

At present, the disposable liquid collection device typically used in clinical practices consists of a simple disposable liquid collection cup and a disposable liquid collection tube. Patients were provided with a liquid collection tube and a plastic collection cup in the hospital. The patient first goes to the toilet and uses the plastic collection cup to collect the liquid, then pours the collected liquid into the liquid collection tube and cover the tube cap after reaching the required volume of the liquid. Since the current collected process is completed step by step, it causes some problems, such as liquid splash and spillage, and operation inconvenience. The unsanitary collection of the liquid may lead to an inaccurate result of laboratory examination, which don't reflect the patient's physical condition. When exposed to the external environment, the liquid samples are easily polluted by foreign materials and bacteria. Additionally, it is extremely likely for patients and medical workers to contact with pathogenic liquid samples and encounter a high safety risk.

The latest disposable liquid collection devices consist of a liquid collection tube and a liquid collector. After the completion of sample collection, it is necessary for the patients or medical workers to put on the cover of the liquid collection tube, which increases the risk of cross-infection. In addition, as some collection devices are used vertically, it is not convenient for women to collect liquid.

Medical Liquid Collector (Chinese patent number: 201620428875.6; application date: May 12, 2016) discloses a medical liquid collector, which consists of a jug body for containing the retained liquid, a jug cover mounted at a spout of the jug body, a sampling port disposed on the outer wall of the jug body for extracting liquid in the jug, and a sealing cap mounted at the sampling port for sealing the sampling port. This medical liquid collector has a simple structure for convenient use. Thus, it is suitable for patients who need to collect multiple urine specimens for total measurement or need to measure and test. Besides, it has been demonstrated that it does not dirty the operator's hands when collecting urine, and that it also does not spill the collected urine, and that it is easy to retain a urine sample that needs to be tested.

Liquid Collector (Chinese patent number: 201620867655.3; application date: Aug. 10, 2016) discloses a liquid collector, which includes a liquid collecting device, a connect component and a liquid storing tube. The liquid collecting device and the liquid storing tube are detachably connected through the connect component. The liquid collecting device has a liquid collecting cavity and the liquid storing tube has a liquid storing cavity. The connect component includes a connecting tube. The liquid collecting cavity is connected with the liquid storing cavity through the connecting tube. In this liquid collector, after collecting liquid in the liquid collecting cavity of the liquid collecting device, the liquid flows into the liquid storing cavity of the liquid storing tube through the connecting tube. In the liquid collecting process, it does not require manual pouring of the liquid. The collecting operation is simple, and liquid leakage or polluting an outer wall of the liquid storing tube is avoided. After the convenient liquid collection is completed, the liquid storing tube is separated from the liquid collecting device, and then sent for examination. In addition, a quantitative control device is used for conveniently obtaining a quantitative liquid, so that the amount of the sample volume is accurate, and is neither too much nor too little, which is convenient for subsequent examination.

The medical liquid collector (Chinese patent number: 201620428875.6) mentioned above has some advantages as follows. Firstly, it has a simple and convenient structure, especially for patients who need to collect multiple urine specimens for total measurement or need to measure and test. Secondly, it does not dirty the operator's hands when collecting urine. Finally, it does not spill the collected urine, and is easy to retain a urine sample that needs to be tested. In the liquid collector (Chinese patent number: 201620867655.3), after collecting liquid in the liquid collecting cavity of the liquid collecting device, the liquid flows into the liquid storing cavity of the liquid storing tube through the connecting tube. In this liquid collecting process, it does not require manual pouring of the liquid. The collecting operation is simple, and liquid leakage or polluting an outer wall of the liquid storing tube can be avoided. After the convenient liquid collection is completed, the liquid storing tube is separated from the liquid collecting device, and then sent for examination. In addition, a quantitative control device is used for conveniently obtaining a quantitative liquid, so that the amount of the sample volume is accurate, and is neither too much nor too little, which is convenient for subsequent examination. However, so far, it has not been reported about a portable liquid collection device that directly collects the liquid sample into a closed collection tube without secondary dispensing in a relatively enclosed environment, and that is capable of reducing the cross-infection and increasing the accuracy of test results, and that is position-free and leakage-free, user-friendly for the medical workers after the liquid collection is completed.

Therefore, it is extremely urgent to develop a portable liquid collection device that directly collects the liquid sample into an enclosed collection tube without secondary dispensing in a relatively enclosed environment, and that is also capable of reducing the cross-infection and increasing the accuracy of test results, and that is also position-free and leakage-free, user-friendly for the medical workers after the liquid collection is completed.

SUMMARY

In order to overcome the shortcomings of the prior art, an objective of the present invention is to provide a portable liquid collection device for directly collecting liquid into an enclosed collection tube without secondary dispensing in a relatively enclosed environment. In this collection process, the portable liquid collection device is capable of reducing the cross-infection and increasing the accuracy of test results. Besides, this portable liquid collection device is also position-free and leakage-free, user-friendly for the medical workers after the liquid collection is completed.

In order to realize the above objective, the present invention adopts the following technical solutions.

The present invention provides a portable liquid collection device that includes a liquid collector, a guide tube and a liquid collection tube. The liquid collector is shaped as a circular opening, and includes the flowing liquid hole and the anti-slip structure.

The guide tube includes two ends, wherein one end connects to the liquid collector, and the other end is in a needle-shaped structure and connects to the liquid collection tube. The guide tube has the outer annular structure. The guide tube is provided with the flowing liquid hole and the flowing gas hole. A liquid channel and a gas channel are disposed in a tube body of the guide tube. The liquid channel connects to the flowing liquid hole, wherein the flowing liquid hole of the guide tube connects to the flowing liquid hole of the liquid collector. The gas channel connects to the flowing gas holes.

The liquid collection tube includes the collection tube body and the collection tube cover. The collection tube body and the collection tube cover are structurally connected through a connection manner. A surface of the collection tube body is provided with scale lines. The collection tube cover includes the tube cover body and the blocking plug. The inner-outer embedding connection structure is formed between the inner wall at the top of the tube cover body and the outer annular structure of the guide tube. The placing slot for placing the blocking plug is disposed between the top of the tube cover body and the bottom of the tube cover body. The diameter of the inner wall at the top of the placing slot is smaller than a diameter of the inner wall at the bottom of the placing slot. The structure of the blocking plug is a three-layer structure. The diameter of an upper plug body is smaller than the diameter of a lower plug body, and the diameter of the upper plug body and the diameter of the lower plug body are smaller than the diameter of the middle plug body. The structure of the blocking plug forms a left and right double annular structure with the upper plug body and the middle plug body in the arc structures. The placing slot is matched with a size and a shape of the middle plug body of the blocking plug. The inner-outer embedding connection structure is formed between the blocking plug and the inner wall of the tube cover body.

As a preferred technical solution, the liquid collector includes at least one flowing liquid hole. The concave surface of the liquid collector is a mesh structure or a dot structure and so on. The anti-slip structure of the surface of the liquid collector is a stripe structure or a dot structure that can form Braille.

As a preferred technical solution, the liquid collector and the guide tube are integrated, or are fixedly connected in a splitting manner. The liquid collector is allowed to be used separately.

As a preferred technical solution, the guide tube is connected to the different connection position of the liquid collector. The guide tube is connected to the connection position of the liquid collector at the different angle. The number of the flowing gas holes is one or more, and the number of the flowing liquid holes is one or more. The number of the gas channels is one or more, and the number of the liquid channels is one or more. The number of the outer annular structures is one or more, and the outer annular structure may be a partial annular structure. The width of an upper end of the outer annular structure is not equal to the width of a lower end of the outer annular structure. The outer annular structure is provided with the outer annular groove, and a surface of the outer annular groove is provided with the flowing gas hole.

As a preferred technical solution, the collection tube body and the collection tube cover need to be structurally connected in a connection manner, that is, the collection tube body is provided with a connection structure, and the collection tube cover is provided with a corresponding connection structure. The connection manner includes but is not limited to a thread connection manner, a snap-fit connection manner or a turning fastening connection manner. The collection tube body and the collection tube cover are provided with the anti-slip structure. The anti-slip structure is a stripe structure or a dot structure that can form Braille.

As a preferred technical solution, the tube cover body has a hollow cylindrical structure or a hollow elliptical structure. The top of the tube cover body is provided with a tube plug. The tube cover body and the tube plug are integrated, or are fixedly connected in a splitting manner. One or more tube cover channels are disposed between the inner wall at the bottom of the tube cover body and the placing slot. One or more annular grooves are disposed between the inner wall at the top of the tube cover body and the placing slot. One or more transverse grooves are disposed on a surface at the top of the tube cover body. One or more elongated grooves are disposed from a surface of the inner wall at the top of the tube cover body to a surface of the annular grooves. The annular grooves, the transverse grooves and the elongated grooves connect to each other.

As a preferred technical solution, the upper plug body and the middle plug body of the blocking plug are tightly combined with the tube cover body, and the diameter of the lower plug body of the blocking plug is matched with the inner diameter of a tube port of the collection tube body. The blocking plug forms a one-layer or dual-layer hollow annular structure. The blocking plug includes but is not limited to a rubber plug.

As a preferred technical solution, when the liquid collector, the guide tube and the liquid collection tube are used in combination, the needle-shaped structure of the guide tube penetrates the blocking plug of the collection tube cover to enter the collection tube body. After the inner-outer embedding connection between the outer annular structure of the guide tube and the inner wall at the top of the tube cover body of the liquid collection tube is completed, liquid and air are in a flowing state. In this flowing state, the liquid first flows into the liquid collector, and then flows into the liquid collection tube via the guide tube, and the air in the liquid collection tube flows out of the liquid collection tube via the guide tube.

As a preferred technical solution, the flowing state includes a liquid flowing state and an air flowing state. The liquid flowing state includes a state in which the liquid flows into the flowing liquid hole of the liquid collector, then flows out of the flowing liquid hole of the guide tube via the liquid channel, and finally flows into the liquid collection tube. The air flowing state includes a state in which the air in the liquid collection tube flows into the flowing gas hole of the guide tube, then flows out of the flowing gas hole of the guide tube via the gas channel, and finally flows into the ambient.

As a preferred technical solution, in the air flowing state, the air in the liquid collection tube flows out of the flowing gas hole and then directly flows into the ambient, alternatively, the air in the liquid collection tube flows out of the flowing gas hole, and then flows into the ambient via an air flowing path formed by connected annular grooves, elongated grooves and transverse grooves.

Advantages of the present invention are as follows:

1. The liquid collector is shaped as a semi-elliptical opening shape and provided with a mesh structure on the concave surface, which is not only convenient for men or women to use for urine collection, but also can avoid liquid splashing in the liquid collection process, thereby effectively ensuring the sanitation during collection.

2. The design of the placing slot in the tube cover body can effectively prevent the blocking plug from falling off or being removed due to different applied forces when the needle-shaped structure at the front end of the guide tube gets in or out of the collection tube body, which facilitates operators to use.

3. The front end of the guide tube is designed as the needle-shaped structure to conveniently enter into the collection tube body by penetrating the blocking plug in the collection tube cover. The blocking plug plays a certain fixing role. The outer annular structure of the rear end of the guide tube and the inner wall at the top of the tube cover body are connected in an inner-outer embedding manner, which plays a secondary fixing role, thereby facilitating the liquid collection.

4. The rear end of the guide tube is obliquely connected to the liquid collector at a certain angle. During the liquid collection process, the liquid collector in a horizontally placed state can smoothly collect the liquid, and the liquid flows into the guide tube along a certain descending slope and then enters into the liquid collection tube, which is conducive for the user to naturally hold the liquid collection tube with hands.

5. The width is not equal between the upper end and the lower end in the outer annular structure, which ensures the smoothness of the liquid collection process. The inner-outer embedding connection between the inner wall of the top of the tube cover body and the outer annular structure of the rear end of the guide tube is used in the liquid collection process, so that the tube cover body does not completely cover the outer annular structure of the guide tube. Accordingly, there is always an air gap for the gas in the liquid collection tube to flow in the outer annular groove located in the outer annular structure, and the gas in the liquid collection tube can smoothly flow into the ambient.

6. The collection tube cover includes the blocking plug. The diameter of the lower plug body of the blocking plug is adapted to the inner diameter of the tube port of the collection tube body. The lower plug body of the blocking plug is fixedly connected to the tube port of the collection tube body in an inner-outer friction fitting manner, so as to ensure the fixing function and ensure the seal in the liquid collection process to avoid liquid leakage at the same time.

7. The collection tube cover can be fixedly connected to the collection tube body by adopting the inner-outer friction fitting manner, the thread connection manner, the snap-fit connection manner or the turning fastening connection manner. The collection tube cover and the collection tube body can be fixed only by simple operations in the fixing process, ensuring that the connection between the collection tube cover and the collection tube body has good tightness and is not easy to loosen.

8. The design of the left and right double annular structure of the blocking plug not only can ensure that the blocking plug will not fall off the fixed placing slot due to the external force when the needle-shaped structure of the front end of the guide tube is inserted into or pulled out, but also can prevent the needle-shaped structure of the front end of the guide tube from being excessively deeply inserted.

9. The diameter of the inner wall at the top of the placing slot is smaller than the diameter of the inner wall at the bottom of the placing slot. The blocking plug has the arc structure in the upper and middle plug bodies. The inner diameter of the tube port of the collection tube body is larger than the diameter of the inner wall at the top of the placing slot and smaller than the diameter of the inner wall at the bottom of the placing slot, which facilitates fixing the blocking plug connected to the collection tube body to the placing slot.

10. The liquid collection tube does not require a negative pressure in the liquid collection process. After the liquid collection is completed, the excess liquid in the liquid collector is poured out and then the guide tube can be directly pulled out. Using the surface tension of the liquid, the liquid collected in the liquid collector does not easily flow out when the excess liquid is poured out. In addition, using the fixing function between the collection tube cover and the collection tube body, the liquid in the liquid collection tube does not easily flow out, thereby enabling medical technicians to conveniently handle and transport after collection.

11. The liquid is directly collected into the liquid collection tube, and the liquid collection process is completed at one time without secondary dispensing, which reduces the risk of cross-infection and improves the sanitation and convenience of liquid collection.

12. Surfaces of the liquid collector and the liquid collection tube are provided with stripe or dot anti-slip structures that can form Braille, which is user-friendly for the blind person to use the device.

13. Using the design of the tube plug in the collection tube cover can maintain the aseptic environment of the inner portion at the top of the tube cover body and the blocking plug before the needle-shaped structure of the guide tube is not inserted into the collection tube body. After the needle-shaped structure of the guide tube is inserted into the blocking plug to enter the collection tube body, when the liquid collection is completed, the guide tube is pulled out and then the tube plug is covered, which can avoid liquid leakage due to bad sealing property of the blocking plug.

14. The tube cover channel in the collection tube cover is matched with the connection structure disposed on the collection tube body, which facilitates the collection tube body to enter the collection tube cover and then be fixed to the placing slot.

Reference signs and components involved in the figures are as follows:

| | |
|---|---|
| 1. liquid collector | 11. anti-slip structure |
| 12. mesh structure | 2. guide tube |
| 21. needle-shaped structure | 22. outer annular structure |
| 221. outer annular groove | 23. flowing liquid hole |
| 24. flowing gas hole | 25. liquid channel |
| 26. gas channel | 3. liquid collection tube |
| 31. collection tube body | 311. scale line |
| 32. collection tube cover | 321. tube cover body |
| 3211. placing slot | 3212. tube plug |
| 3213. tube cover channel | 3214. thread structure |
| 3215. snap-fit structure | 3216. turning fastening structure |
| 3217. annular groove | 3218. elongated groove |
| 3219. transverse groove | 322. blocking plug |
| 3221. arc structure | |

DETAILED DESCRIPTION OF THE EMBODIMENTS

The specific embodiments provided by the present invention will be explained in detail below in conjunction with the drawings.

Embodiment 1

Figure 1:
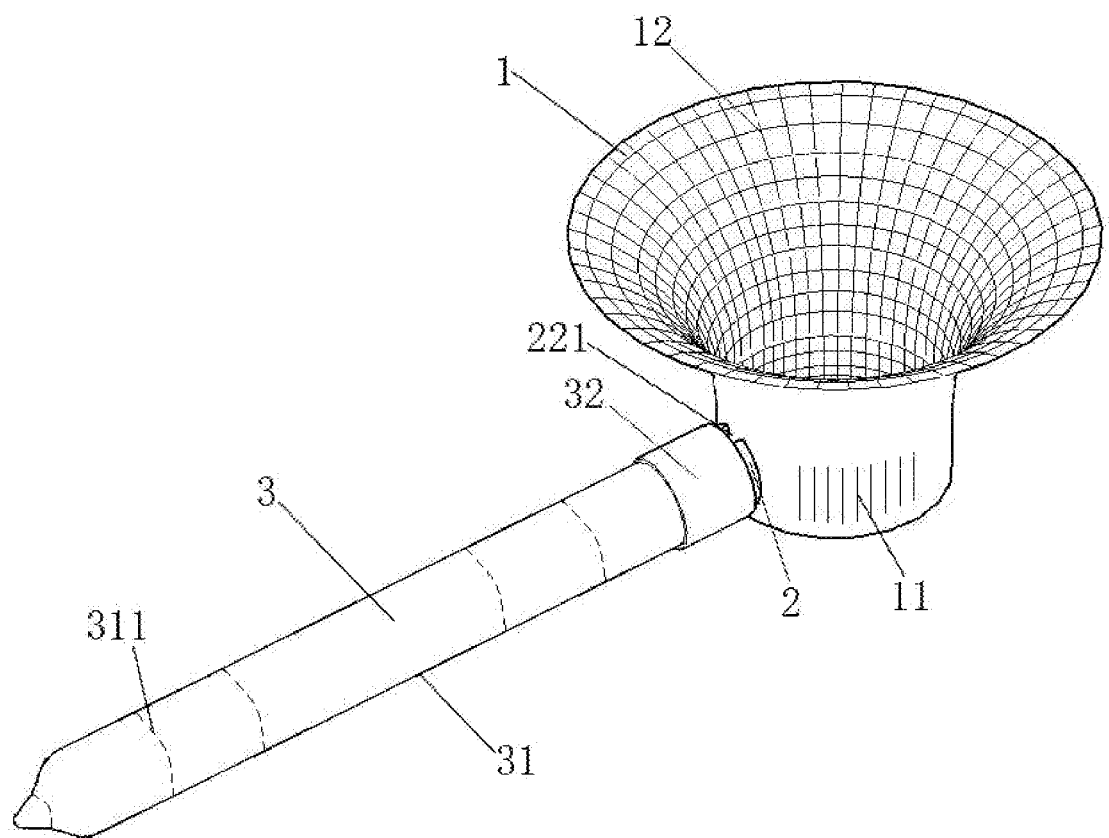
FIG. 1 shows an overall schematic diagram of a portable liquid collection device in which a liquid collector, a guide tube and a liquid collection tube are connected according to the present invention.

Referring to FIG. 1, FIG. 1 shows an overall schematic diagram of a portable liquid collection device in which a liquid collector, a guide tube and a liquid collection tube are connected according to the present invention. A portable liquid collection device includes the liquid collector 1, the guide tube 2 and the liquid collection tube 3. The liquid collector 1 is shaped as a circular opening, and the liquid collector 1 is provided with the flowing liquid hole 23 (not shown in FIG. 1) and the anti-slip structure 11. The liquid collector 1 is further provided with the mesh structure 12.

Figure 2A:
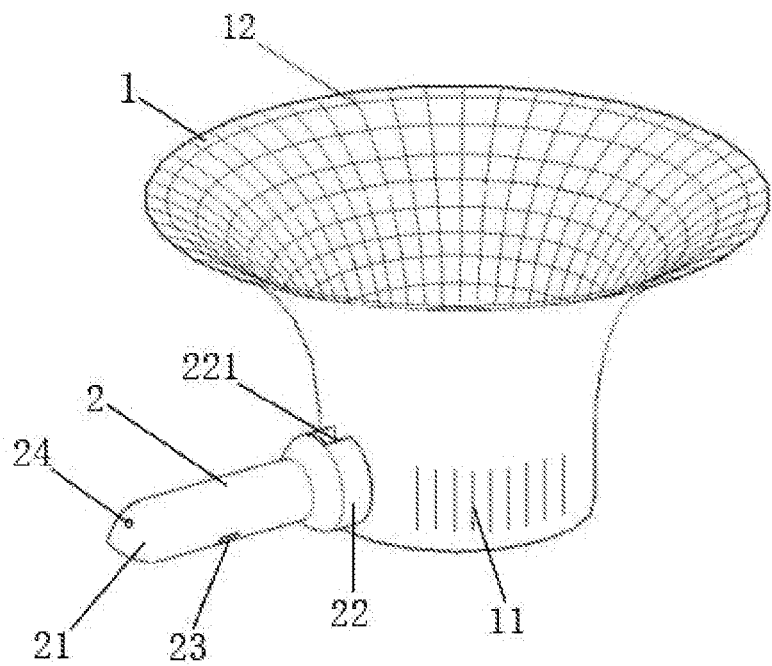
FIG. 2A shows a stereoscopic structure diagram of the portable liquid collection device in which a liquid collector and a guide tube are integrally connected according to the present invention.
Figure 2B:
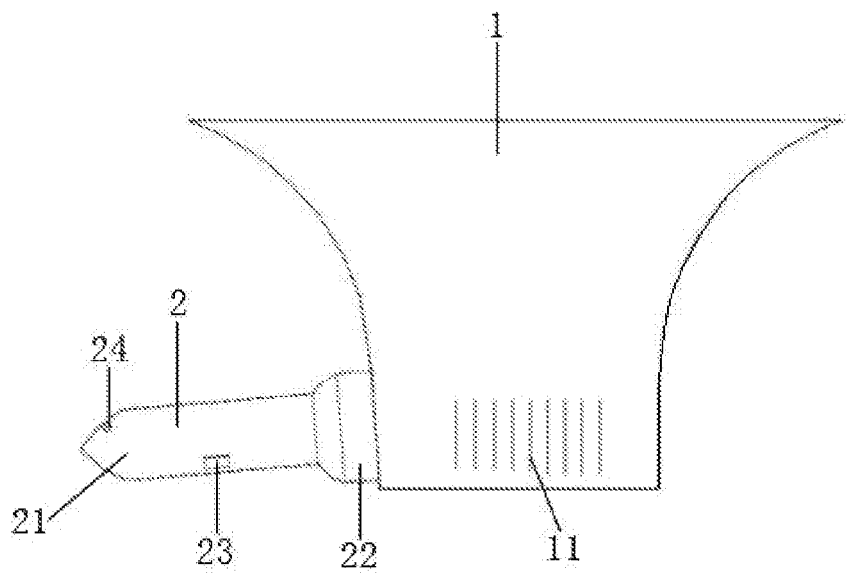
FIG. 2B shows a front view of the portable liquid collection device in which the liquid collector and the guide tube are integrally connected according to the present invention.
Figure 3:
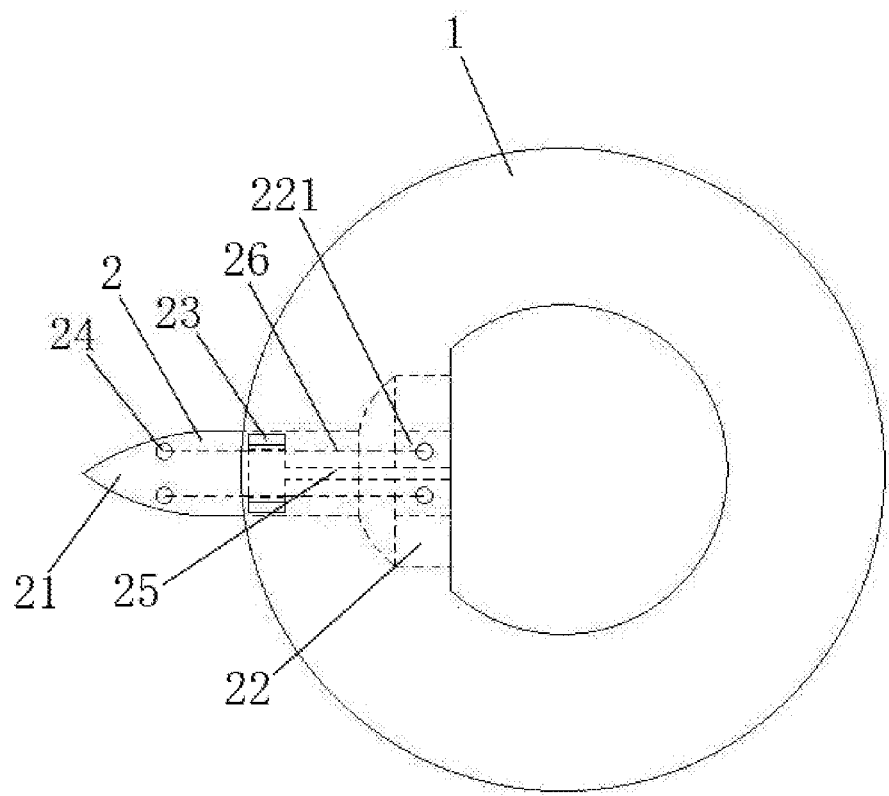
FIG. 3 shows a top view of the portable liquid collection device in which a liquid collector and a guide tube are integrally connected according to the present invention.

Referring to FIGS. 2A-3, FIG. 2A shows a stereoscopic structure diagram and a front view of the portable liquid collection device in which the liquid collector and the guide tube are integrally connected according to the present invention; FIG. 2B shows a front view of the portable liquid collection device in which the liquid collector and the guide tube are integrally connected according to the present invention. FIG. 3 shows a top view of the portable liquid collection device in which the liquid collector and the guide tube are integrally connected according to the present invention. As shown in FIGS. 2A-2B, the guide tube 2 includes two ends, one end connects to the liquid collector 1 (not shown in FIGS. 2A-2B), and the other end is in the needle-shaped structure 21 and connects to the liquid collection tube 3 (not shown in FIGS. 2A-2B). As shown in FIG. 3, the guide tube 2 is provided with the outer annular structure 22. The outer annular structure 22 is provided with the outer annular groove 221, and the surface of the outer annular groove 221 is provided with the flowing gas hole 24. The guide tube 2 is provided with the flowing liquid hole 23 and the flowing gas hole 24, and the liquid channel 25 and the gas channel 26 are disposed in the tube body of the guide tube 2. The liquid channel 25 connects to the flowing liquid hole 23. Specifically, the flowing liquid hole 23 of the guide tube 2 is configured to connect to the flowing liquid hole 23 of the liquid collector 1 (not shown in FIG. 3). The gas channel 26 connects to the flowing gas hole 24.

Figure 4:
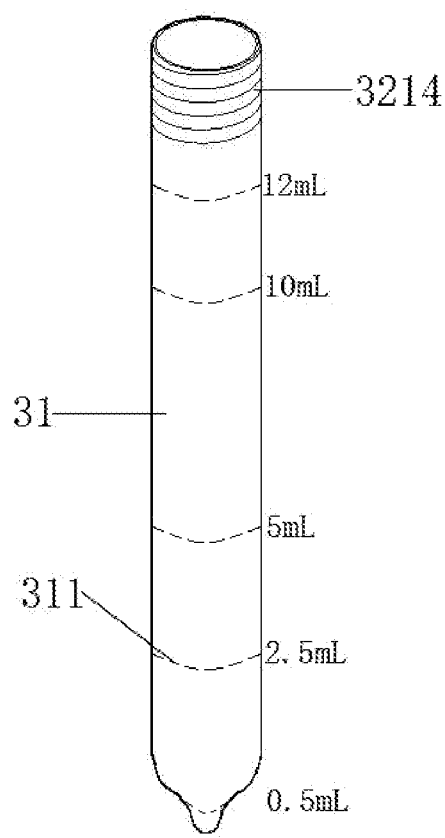
FIG. 4 shows a stereoscopic structure diagram of a collection tube body in the portable liquid collection device according to the present invention.
Figure 5A:
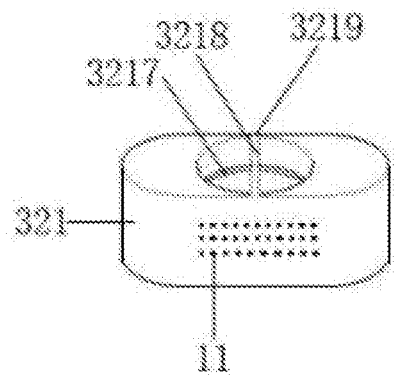
FIG. 5A shows a stereoscopic structure diagram of the upper portion of a tube cover body of the collection tube cover in the portable liquid collection device according to the present invention.
Figure 5B:
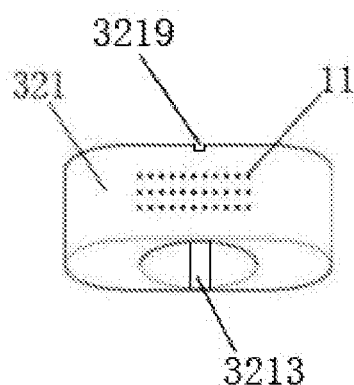
FIG. 5B shows a stereoscopic structure diagram of the lower portion of the tube cover body of the collection tube cover in the portable liquid collection device according to the present invention.
Figure 5C:
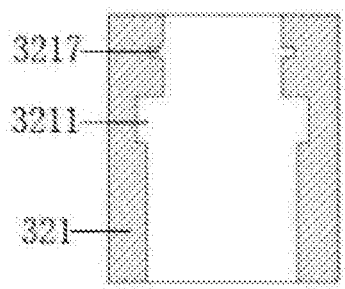
FIG. 5C shows an overall plane diagram of the tube cover body of the collection tube cover in the portable liquid collection device according to the present invention.
Figure 5D:
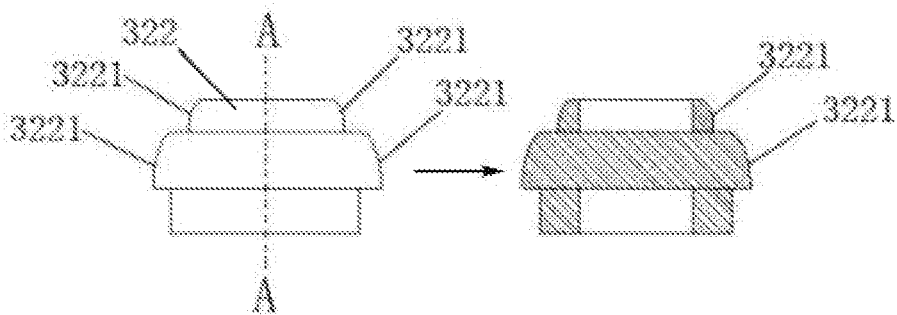
FIG. 5D shows a plan and cross-sectional (line A-A) diagram of a blocking plug of the collection tube cover in the portable liquid collection device according to the present invention.
Figure 5E:
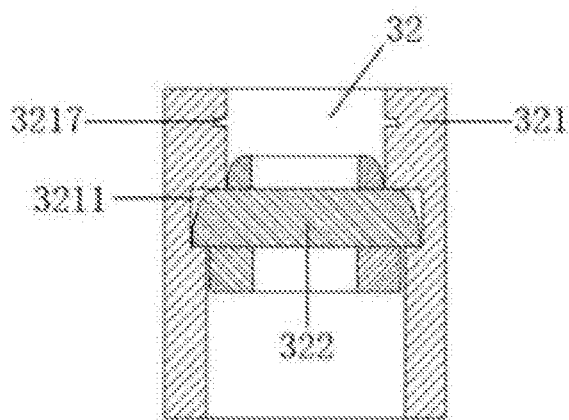
FIG. 5E shows a diagram showing the assembly of the tube cover body and the blocking plug of the collection tube cover in the portable liquid collection device according to the present invention.

Referring to FIG. 4 and FIGS. 5A-5E, FIG. 4 shows a stereoscopic structure diagram of a collection tube body in the portable liquid collection device according to the present invention. FIGS. 5A-5E show structure diagrams of a collection tube cover in the portable liquid collection device according to the present invention, wherein FIG. 5A shows a stereoscopic structure diagram of the upper portion of a tube cover body; FIG. 5B shows a stereoscopic structure diagram of the lower portion of the tube cover body; FIG. 5C shows an overall plane diagram of the tube cover body; FIG. 5D shows a plan and a cross-sectional (line A-A) diagram of a blocking plug of the collection tube cover in the portable liquid collection device according to the present invention; and FIG. 5E shows a diagram showing the assembly of the tube cover body and the blocking plug of the collection tube cover in the portable liquid collection device according to the present invention. The liquid collection tube 3 includes the collection tube body 31 and the collection tube cover 32. The collection tube body 31 and the collection tube cover 32 can be structurally connected through a specific connection manner. As shown in FIG. 4, the surface of the collection tube body 31 is provided with the scale lines 311 and the thread structure 3214. As shown in FIGS. 5A-5E, the collection tube cover 32 includes the tube cover body 321 and the blocking plug 322. The tube cover body 321 is provided with the anti-slip structure 11. The anti-slip structure 11 is a dot structure, and the dot structure may form Braille. The placing slot 3211 for placing the blocking plug 322 is disposed between the top and the bottom of the tube cover body 321. The placing slot 3211 is matched with the size and shape of the middle plug body of the blocking plug 322. The tube cover channel 3213 is disposed between the inner wall at the bottom of the tube cover body 321 and the placing slot 3211. The diameter of the inner wall at the top of the placing slot 3211 is smaller than the diameter of the inner wall at the bottom of the placing slot 3211. The structure of the blocking plug 322 is a three-layer structure. The diameter of the upper plug body is smaller than the diameter of the lower plug body, and the diameter of the upper plug body and the diameter of the lower plug body are smaller than the diameter of the middle plug body to form a left-right double annular structure. Two sides of each of the upper plug body and the middle plug body of the blocking plug 322 are the arc structure 3221.

Figure 6:
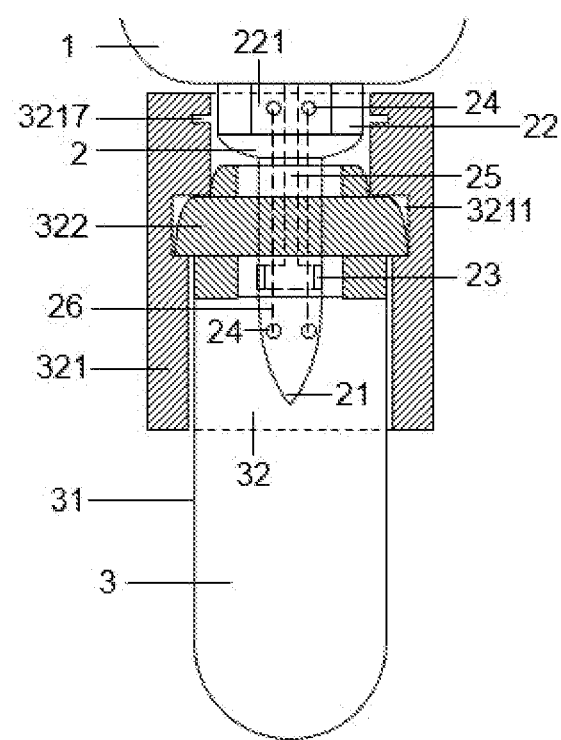
FIG. 6 shows a partial plane diagram of a portable liquid collection device in which a liquid collector, a guide tube and a liquid collection tube are connected according to Embodiment 1 of the present invention.

Referring to FIG. 6, FIG. 6 is a partial plane diagram of a portable liquid collection device in which the liquid collector, the guide tube and the liquid collection tube are connected according to Embodiment 1 of the present invention. In the present embodiment, an inner-outer embedding connection structure is formed between the blocking plug 322 and the inner wall of the tube cover body 321. The inner-outer embedding connection structure is formed between the outer annular structure 22 of the guide tube 2 and the inner wall of the top of the tube cover body 321. An inner-outer friction fitting and fixing structure is formed between the lower plug body of the blocking plug 322 of the collection tube cover 32 and the tube port of the collection tube body 31. The flowing liquid hole 23 is disposed at the middle of the bottom of the guide tube 2. The flowing gas hole 24 is disposed at the top of the front end of the guide tube 2 and the rear end of the guide tube 2. The annular groove 3217 is disposed between the inner wall of the top of the tube cover body 321 and the placing slot 3211. Two transverse grooves 3219 (not shown in FIG. 6) are disposed on the surface of the top of the tube cover body 321. Two elongated grooves 3218 (not shown in FIG. 6) are disposed from the surface of the inner wall of the top of the tube cover body 321 to the surface of the annular groove 3217. The annular groove 3217, the transverse grooves 3219 and the elongated grooves 3218 connect to each other.

As shown in FIG. 6, when the liquid collector 1, the guide tube 2 and the liquid collection tube 3 are used in combination, the needle-shaped structure 21 of the guide tube 2 penetrates the blocking plug 322 of the collection tube cover 32 to enter the collection tube body 3. After the inner-outer embedding connection between the outer annular structure 22 of the guide tube 2 and the inner wall of the top of the tube cover body 321 of the liquid collection tube 3 is completed, liquid and air are in a flowing state. In the flowing state, the liquid first flows into the liquid collector 1, and then flows into the liquid collection tube 3 via the guide tube 2, and the air in the liquid collection tube 3 flows out of the liquid collection tube 3 via the guide tube 2. In the liquid flowing state and the air flowing state during the liquid collection process, the liquid flows into the flowing liquid hole 23 (not shown in FIG. 6) of the liquid collector 1, then flows out of the flowing liquid hole 23 of the guide tube 2 via the liquid channel 25, and finally flows into the liquid collection tube 3. The air in the liquid collection tube 3 flows into the flowing gas hole 24 of the guide tube 2, flows out of the flowing gas hole 24 of the guide tube 2 via the gas channel 26, and then flows into the ambient via an air flowing path formed by the communicated annular grooves 3217, elongated grooves 3218 and transverse grooves 3219. The rear end of the guide tube 2 is obliquely connected to the side surface of the liquid collector 1 at a certain angle. In the liquid collection process, the liquid flows into the guide tube 2 along a certain descending slope and then enters into the liquid collection tube 3, which is conducive for the user to naturally hold the liquid collection tube 3 with hands, while the liquid collector 1 in a horizontally placed state can smoothly collect the liquid. In addition, due to the action of gravity, when liquid flows into the liquid collection tube 3 from the flowing liquid hole 23 disposed in the middle of the bottom of the guide tube 2, the liquid will not block the flowing gas hole 24 disposed in the upper position of the top of the guide tube 2, Moreover, by using the design of the structure of the outer annular groove 221, and using the air flowing path formed by the annular grooves 3217, the transverse grooves 3219 and the elongated grooves 3218, the smoothness of the air flowing can be effectively ensured. The outer annular groove 221 can also be in a trapezoidal structure, and the flowing gas holes 24 are disposed on two side surfaces of the outer annular groove 221. The purpose of this design is to ensure that the flowing gas holes 24 in the outer annular groove 221 are free from contamination or blockage.

As it should be noted, the liquid collected by the present invention includes but not is limited to urine. As long as the liquid can enter into the guide tube via the liquid collector of the present invention and finally flow into the liquid collection tube, these liquids all can be used as the collection targets of the collection device in the present invention. The blocking plug 322 includes but is not limited to a rubber plug. When the blocking plug 322 is placed, the lower plug body of the blocking plug 322 is first fixed to the tube port of the liquid collection tube 3 in an inner-outer fitting manner, and the liquid collection tube 3 is gradually moved into the tube cover body 321. The friction effect between the arc structures 3221 on two sides of the upper and middle plug bodies of the blocking plug 322 and the tube cover body 321 is used, and the elasticity of the blocking plug 322 itself and the design of the structure of the placing slot 3211 are used, so that squeezing forces acting on the placing slot 3211 from two sides and upper and lower sides of the blocking plug 322 cancel out the squeezing forces acting on the blocking plug 322 from left, right, upper and lower sides of the placing slot 3211, thereby ensuring that the blocking plug 322 will not fall off after being fixed to the placing slot 3211.

The tube cover body 321 may be in a hollow elliptical structure, and two sides of the short diameter of the tube cover body 321 are in planar structures. The two sides of the tube cover body 321 are disposed in planar structures, which facilitates disposing the anti-slip structure 11 with a dot shape to enable dots to form Braille, thereby facilitating visually blind persons to recognize and use. The top of the tube cover body 321 is provided with the tube plug 3212. The tube plug 3212 may be integrally fixed to a side surface of the top of the tube cover body 321 by using a tie or other connecting bands, or be fixedly connected to the surface of the top of the tube cover body 321 in a splitting manner. The design of the placing slot 3211 in the tube cover body 321 can effectively prevent the blocking plug 322 from falling off or being removed caused due to different applied forces when the needle-shaped structure 21 of the front end of the guide tube 2 enters the collection tube body 31, which facilitates operators to use. Designed as the needle-shaped structure 21, the front end of the guide tube 2 can conveniently penetrate the blocking plug 322 in the collection tube cover 32, then enter into the collection tube body 31. The blocking plug 322 plays a certain fixing role. The outer annular structure 22 of the rear end of the guide tube 2 and the inner wall of the top of the tube cover body 321 are connected in an inner-outer embedding manner, which plays a secondary fixing role, thereby facilitating the liquid collection.

The number of the flowing gas holes 24 is one or more, and the number of the flowing liquid holes 23 is one or more. The number of the gas channels 26 is one or more, and the number of the liquid channels 25 is one or more. The number of the outer annular structures 22 is one or more, and the outer annular structure 22 may be a partial annular structure. The width of the upper end of the outer annular structure 22 may be not equal to the width of the lower end of the outer annular structure 22. The sizes and shapes of the flowing gas hole 24 and the flowing liquid hole 23 may be disposed as needed. By means of the design that the width of the upper end of the outer annular structure 22 may be not equal to the width of the lower end of the outer annular structure 22, the inner-outer embedding connection between the outer annular structure 22 and the inner wall of the top of the tube cover body 321 is used in the liquid collection process, so that the tube cover body 321 does not completely cover the outer annular structure 22 of the guide tube 2. Accordingly, the outer annular groove 221 in the outer annular structure 22 always leaves a gap for air flowing, and the air in the liquid collection tube 3 can smoothly flow into the ambient, which ensures the smoothness of the liquid collection process. The blocking plug 322 is disposed in the collection tube cover 32. The diameter of the lower plug body of the blocking plug 322 is adapted to the inner diameter of the tube port of the collection tube body 31. The lower plug body of the blocking plug 322 is fixedly connected to the tube port of the collection tube body 31 in an inner-outer friction fitting manner, so as to ensure the fixing function and ensure the seal in the liquid collection process to avoid liquid leakage at the same time. The design of the left and right double annular structure of the blocking plug 322 not only can ensure that the blocking plug 322 will not fall off the fixed collection tube cover 32 due to the external force when the needle-shaped structure 21 of the front end of the guide tube 2 is inserted into or pulled out, but also can prevent the needle-shaped structure 21 of the front end of the guide tube 2 from being excessively deeply inserted. The diameter of the inner wall at the top of the placing slot 3211 is smaller than the diameter of the inner wall at the bottom of the placing slot 3211. Two sides of the upper and middle plug bodies of the blocking plug 322 are designed in arc structures 3221. The inner diameter of the tube port of the collection tube body 31 is larger than the diameter of the inner wall at the top of the placing slot 3211 and smaller than the diameter of the inner wall at the bottom of the placing slot 3211, which facilitates fixing the blocking plug 322 connected to the collection tube body 31 to the placing slot 3211. The liquid collection tube 3 does not require a negative pressure in the liquid collection process. After the liquid collection is completed, the excess liquid in the liquid collector 1 is poured out and then the guide tube 2 can be directly pulled out. Using the surface tension of the liquid can ensure that the liquid collected in the liquid collector 1 does not easily flow out when the excess liquid is poured out.

In addition, using the fixing function between the collection tube cover 32 and the collection tube body 31 can ensure that the liquid in the liquid collection tube 3 does not easily flow out, thereby facilitating the medical workers to carry and place. The tube cover channel 3213 in the collection tube cover 32 is matched with the connection structure disposed on the collection tube body 31, which facilitates the collection tube body 31 to enter the collection tube cover 32 and then be fixed to the placing slot 3211. The liquid is directly collected into the liquid collection tube 3, and the liquid collection process is completed at one time without secondary dispensing, which reduces the risk of cross contamination and improves the sanitation and convenience of liquid collection.

Embodiment 2

Figure 7:
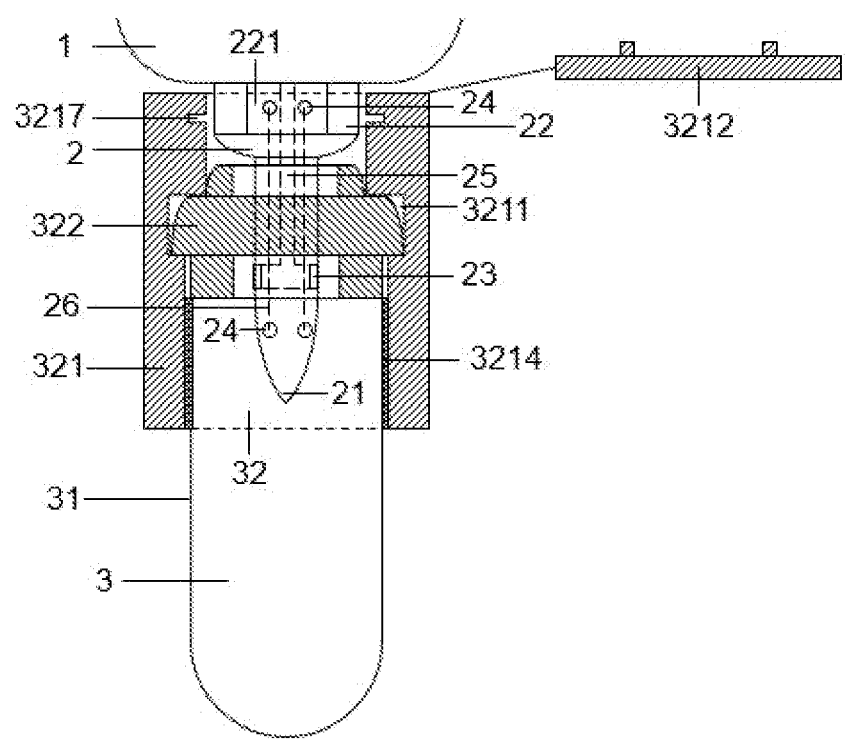
FIG. 7 shows a partial plane diagram of a portable liquid collection device in which a liquid collector, a guide tube and a liquid collection tube are connected according to Embodiment 2 of the present invention.

Referring to FIG. 7, FIG. 7 is a partial plane diagram of a portable liquid collection device in which the liquid collector, the guide tube and the liquid collection tube are connected according to Embodiment 2 of the present invention. The present embodiment is similar to Embodiment 1, while the difference therebetween is as follows: in the present embodiment, the collection tube body 31 is fixed to the collection tube cover 32 using a connection manner of the thread structure 3214. The inner side at the bottom of the collection tube cover 32 and the outer periphery of the tube port of the collection tube body 31 are respectively provided with the thread structures 3214 matching with each other. The tube plug 3212 is disposed at the top of the tube cover body 321. The tube plug 3212 and the side surface of the top of the tube cover body 321 are integrally fixed using the tie. The collection tube body 31 and the collection tube cover 32 are connected by the thread structure to increase the fixation and seal. Using the design of the tube plug 3212 in the collection tube cover 32 can maintain the aseptic environment of the inner portion at the top of the tube cover body 321 and the blocking plug 322 after the collection tube cover 32 is connected to the collection tube body 31 and before the needle-shaped structure 21 at the front end of the guide tube 2 is not inserted into the collection tube body 31. After the needle-shaped structure 21 at the front end of the guide tube 2 is inserted into the blocking plug 322 to enter the collection tube body 31, when the liquid collection is completed, the guide tube 2 is pulled out and then the tube plug 3212 is covered, which can avoid liquid leakage caused due to possible poor seal of the blocking plug 322.

Embodiment 3

Figure 8:
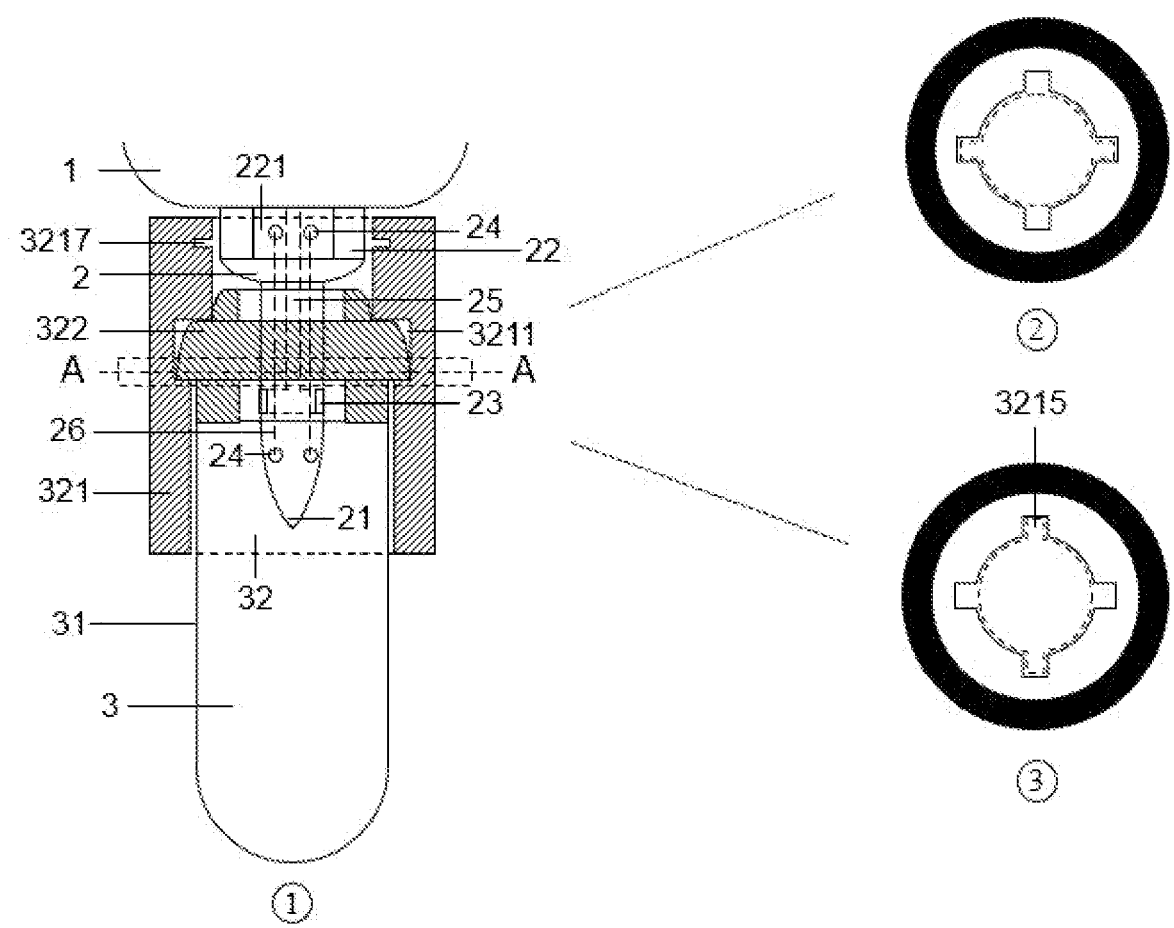
FIG. 8 shows a partial plane diagram of a portable liquid collection device in which a liquid collector, a guide tube and a liquid collection tube are connected according to Embodiment 3 of the present invention.

Referring to FIG. 8, FIG. 8 shows a partial plane diagram of a portable liquid collection device in which the liquid collector, the guide tube and the liquid collection tube are connected according to Embodiment 3 of the present invention (wherein ① shows a partial plane diagram of the portable liquid collection device after the liquid collector 1, the guide tube 2 and the liquid collection tube 3 are connected; ② shows a dotted line A-A cross-sectional view of a schematic diagram of the snap-fit connection between the collection tube body 31 and the collection tube cover 32 when the collection tube body 31 starts to enter the placing slot 3211; and ③ shows a dotted line A-A cross-sectional view of a schematic diagram of the snap-fit connection between the collection tube body 31 and the collection tube cover 32 after the collection tube body 31 ends rotating and is fixed to the placing slot 3211). The present embodiment is similar to Embodiment 1, the difference therebetween is as follows: in the present embodiment, the collection tube body 31 is fixed to the collection tube cover 32 using a connection manner of the snap-fit structure 3215. The inner side at the bottom of the placing slot 3211 and the outer periphery of the tube port of the collection tube body 31 are respectively provided with the snap-fit structures 3215 matching with each other. The collection tube body 31 is fixed to the collection tube cover 32 using the manner of the snap-fit structure 3215, so that and the collection tube body 31 and the collection tube cover 32 can be fixedly connected only by a simple rotation operation when in use. Using the specific connection manner of the snap-fit structure 3215 can avoid possible small debris generated by the friction in the thread connection manner in the fixing process, which ensures the sanitation and tidiness of the collection process. Besides, using the snap-fit connection manner is more convenient to fix.

Embodiment 4

Figure 9:
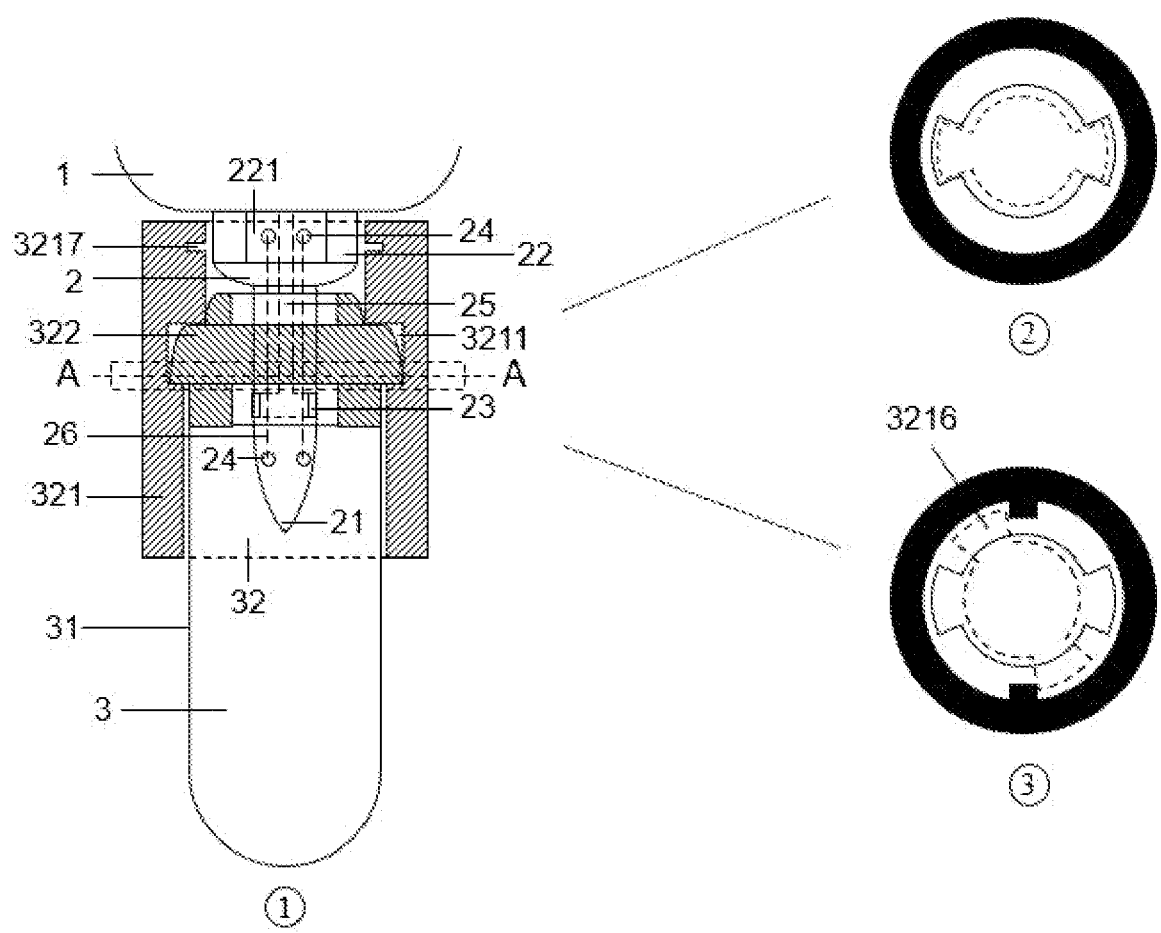
FIG. 9 shows a partial plane diagram of a portable liquid collection device in which a liquid collector, a guide tube and a liquid collection tube are connected according to Embodiment 4 of the present invention.

Referring to FIG. 9, FIG. 9 shows a partial plane diagram of a portable liquid collection device in which the liquid collector, the guide tube and the liquid collection tube are connected according to Embodiment 4 of the present invention (wherein ① shows a partial plane diagram of the portable liquid collection device after the liquid collector 1, the guide tube 2 and the liquid collection tube 3 are connected; ② shows a dotted line A-A cross-sectional view of a schematic diagram of the turning connection between the collection tube body 31 and the collection tube cover 32 when the collection tube body 31 starts to enter the placing slot 3211; and ③ shows a dotted line A-A cross-sectional view of a schematic diagram of the turning connection between the collection tube body 31 and the collection tube cover 32 after the collection tube body 31 ends rotating and is fixed to the placing slot 3211). The present embodiment is similar to Embodiment 1, the difference therebetween is as follows: in the present embodiment, the collection tube body 31 is fixed to the collection tube cover 32 using a connection manner of the turning fastening structure 3216. The bottom of the placing slot 3211 and the surface of the tube port of the collection tube body 31 are provided with the turning fastening structures 3216 matching with each other. The collection tube body 31 is fixed to the collection tube cover 32 using the specific connection manner of the turning fastening structure 3216, so that the connection and fixation can be completed only by a simple rotation operation when in use, and the use is more convenient.

Embodiment 5

Figure 10:
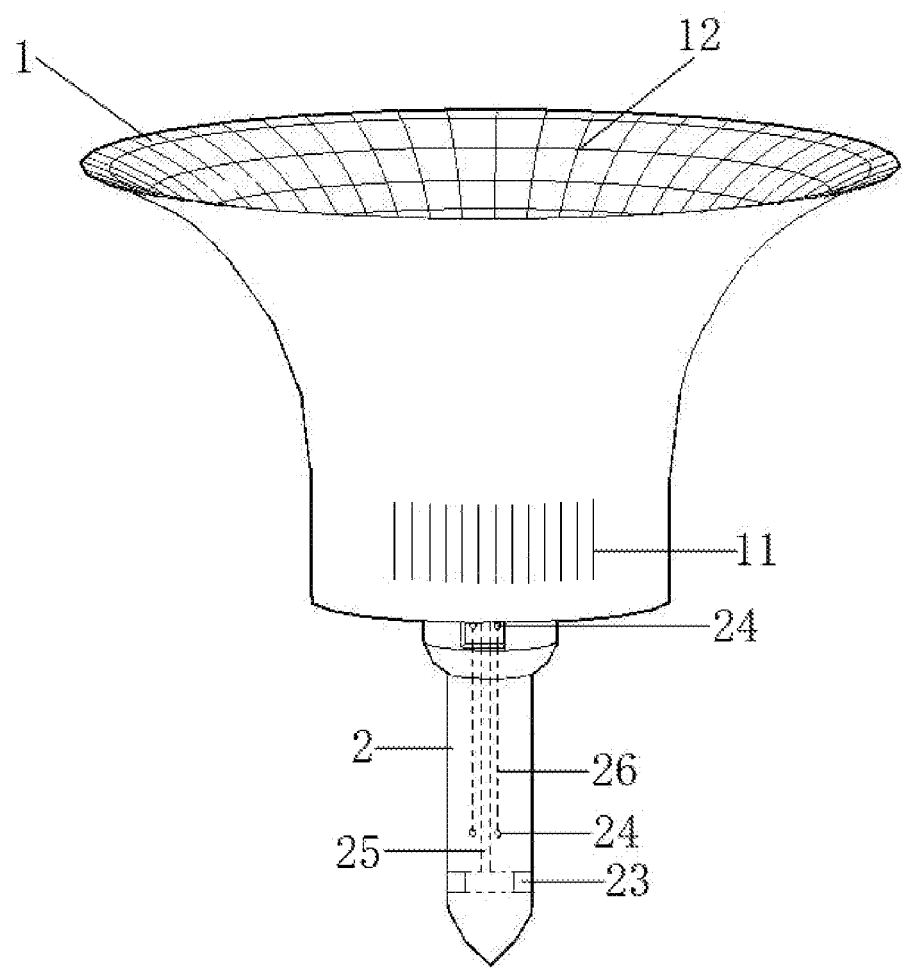
FIG. 10 shows a stereoscopic structure diagram of a portable liquid collection device in which a liquid collector and a guide tube are integrally connected according to Embodiment 5 of the present invention.

Referring to FIG. 10, FIG. 10 shows a stereoscopic structure diagram of an integrated connection between the liquid collector and the guide tube in another portable liquid collection device of the present invention. The present embodiment is similar to Embodiment 1, the difference therebetween is as follows. In the present embodiment, the position of the connection between the guide tube 2 and the liquid collector 1 changes, that is, the guide tube 2 is disposed at the bottom of the liquid collector 1. The angle between the guide tube 2 and the plane at the bottom of the liquid collector 1 changes, that is, the guide tube 2 is vertically connected to the plane at the bottom of the liquid collector 1. The disposed positions of the flowing liquid hole 23 and the flowing gas hole 24 change, wherein the flowing liquid hole 23 is located at the guide tube 2 adjacent to the needle-shaped structure 21, while the flowing gas hole 24 is located above the side surface of the flowing liquid hole 23. The vertical connection between the guide tube 2 and the bottom of the liquid collector 1 can accelerate the liquid collection. The flowing gas hole 24 is disposed above the side surface of the flowing liquid hole 23, so that the liquid will not block the flowing gas hole 24, which will not affect the liquid collection in the liquid collection process. By changing the different connection positions and connection angles between the guide tube 2 and the liquid collector 1, the collection requirements of different liquids can be satisfied.

The present invention provides a portable liquid collection device. The liquid collector is shaped as a semi-elliptical opening shape and provided with a mesh structure on the concave surface, which is not only convenient for men or women to use for urine collection, but also can avoid liquid splashing in the liquid collection process, thereby effectively ensuring the sanitation during collection. The design of the placing slot in the tube cover body can effectively prevent the blocking plug from falling off or being removed caused due to different applied forces when the needle-shaped structure of the front end of the guide tube enters or gets out of the collection tube body, which facilitates operators to use. The front end of the guide tube is designed as the needle-shaped structure to conveniently penetrate the blocking plug in the collection tube cover to enter into the collection tube body. The blocking plug plays a certain fixing role. The outer annular structure of the rear end of the guide tube and the inner wall of the top of the tube cover body are connected in an inner-outer embedding manner, which plays a secondary fixing role, thereby facilitating the liquid collection. The rear end of the guide tube is obliquely connected to the liquid collector at a certain angle. During the liquid collection process, the liquid flows into the guide tube along a certain descending slope and then enters into the liquid collection tube, which is conducive for the user to naturally hold the liquid collection tube with hands, while the liquid collector in a horizontally placed state can smoothly collect the liquid. By means of the design that the width of the upper end of the outer annular structure is not equal to the width of the lower end of the outer annular structure. The inner-outer embedding connection between the inner wall at the top of the tube cover body and the outer annular structure of the rear end of the guide tube is used in the liquid collection process, so that the tube cover body does not completely cover the outer annular structure of the guide tube. Accordingly, the outer annular groove in the outer annular structure always leaves a gap for air flowing, and the gas in the liquid collection tube can smoothly flow into the ambient, which ensures the smoothness of the liquid collection process. The blocking plug is disposed in the collection tube cover. The diameter of the lower plug body of the blocking plug is adapted to the inner diameter of the tube port of the collection tube body. The lower plug body of the blocking plug is fixedly connected to the tube port of the collection tube body in an inner-outer friction fitting manner, so as to ensure the fixing function and ensure the seal in the liquid collection process to avoid liquid leakage at the same time. The collection tube cover can be fixedly connected to the collection tube body by adopting the inner-outer friction fitting manner, the thread connection manner, the snap-fit connection manner or the turning fastening connection manner. The collection tube cover and the collection tube body can be fixed only by simple operations in the fixing process, ensuring that the connection between the collection tube cover and the collection tube body has good tightness and is not easy to loosen. The design of the left and right double annular structure of the blocking plug not only can ensure that the blocking plug will not fall off the fixed placing slot due to the external force when the needle-shaped structure of the front end of the guide tube is inserted into or pulled out, but also can prevent the needle-shaped structure of the front end of the guide tube from being excessively deeply inserted. The diameter of the inner wall at the top of the placing slot is smaller than the diameter of the inner wall at the bottom of the placing slot. Two sides of the upper and middle plug bodies of the blocking plug are designed in arc structures. The inner diameter of the tube port of the collection tube body is larger than the diameter of the inner wall at the top of the placing slot and smaller than the diameter of the inner wall at the bottom of the placing slot, which facilitates fixing the blocking plug connected to the collection tube body to the placing slot. The liquid collection tube does not require a negative pressure in the liquid collection process. After the liquid collection is completed, the excess liquid in the liquid collector is poured out and then the guide tube can be directly pulled out. Using the surface tension of the liquid can ensure that the liquid collected in the liquid collector does not easily flow out when the excess liquid is poured out. In addition, using the fixing function between the collection tube cover and the collection tube body can ensure that the liquid in the liquid collection tube does not easily flow out, thereby enabling medical workers to conveniently handle and transport after collection. The liquid is directly collected into the liquid collection tube, and the liquid collection process is completed at one time without secondary dispensing, which reduces the risk of cross contamination and improves the sanitation and convenience of liquid collection. Surfaces of the liquid collector and the liquid collection tube are provided with stripe or dot anti-slip structures, and the dot structure can form Braille, which enables visually blind persons to use the device. Using the design of the tube plug in the collection tube cover can maintain the aseptic environment of the inner portion at the top of the tube cover body and the blocking plug before the needle-shaped structure at the front end of the guide tube is not inserted into the collection tube body. After the needle-shaped structure at the front end of the guide tube is inserted into the blocking plug to enter the collection tube body, when the liquid collection is completed, the guide tube is pulled out and then the tube plug is covered, which can avoid possible liquid leakage caused due to poor seal of the blocking plug. The tube cover channel in the collection tube cover is matched with the connection structure disposed on the collection tube body, which facilitates the collection tube body to enter the collection tube cover and then be fixed to the placing slot.

These embodiments mentioned above are only preferred embodiments of the present invention. It should be pointed out that improvements and supplements made by those having ordinary skill in this field of technology without departing from the principle of the present invention shall fall within the scope of protection of the present invention.

What is claimed is:

1. A portable liquid collection device, comprising a liquid collector, a guide tube and a liquid collection tube; wherein
    the liquid collector is shaped as a circular opening, and comprises at least a first flowing liquid hole and a first anti-slip structure;
    the guide tube comprises two ends, wherein a first end of the two ends of the guide tube connects to the liquid collector, a second end of the two ends of the guide tube is in a needle-shaped structure, and the second end of the two ends of the guide tube connects to the liquid collection tube; the guide tube is provided with an outer annular structure; the guide tube is provided with a plurality of second flowing liquid holes and a plurality of flowing gas holes; at least a liquid channel and at least a gas channel are disposed in a tube body of the guide tube; the liquid channel connects to at least one of the second flowing liquid holes, wherein at least one of the second flowing liquid holes of the guide tube connects to the first flowing liquid hole of the liquid collector; the gas channel connects to at least one of the flowing gas holes;
    the guide tube is connected to a variable connection position of the liquid collector; the guide tube is connected to the variable connection position of the liquid collector at a variable angle; and the outer annular structure is a partial annular structure; a width of an upper end of the outer annular structure is not equal to a width of a lower end of the outer annular structure; and the outer annular structure is provided with an outer annular groove, and a surface of the outer annular groove is provided with at least one of the plurality of the flowing gas holes; and
    the liquid collection tube comprises a collection tube body and a collection tube cover; the collection tube body and the collection tube cover are structurally connected through a connection manner; a surface of the collection tube body is provided with scale lines; the collection tube cover comprises a tube cover body and a blocking plug; an inner-outer embedding connection structure is formed between an inner wall at a top of the tube cover body and the outer annular structure of the guide tube; a placing slot for placing the blocking plug is disposed between the top of the tube cover body and a bottom of the tube cover body; a diameter of an inner wall at a top of the placing slot is smaller than a diameter of an inner wall at a bottom of the placing slot; a structure of the blocking plug is a three-layer structure, wherein a diameter of an upper plug body is smaller than a diameter of a lower plug body, and the diameter of the upper plug body and the diameter of the lower plug body are smaller than a diameter of a middle plug body; wherein the diameter of the upper plug body forms a left annular structure and the diameter of the lower plug body forms a right annular structure; wherein each of the left annular structure and the right annular structure is an arc structure; the placing slot is matched with the diameter of the middle plug body of the blocking plug; and the inner-outer embedding connection structure is also formed between the blocking plug and an inner wall of the tube cover body.

2. The portable liquid collection device of claim 1, wherein a concave surface of the liquid collector is a mesh structure or a first dot structure; and the first anti-slip structure is a second dot structure, and the second dot structure forms Braille.

3. The portable liquid collection device of claim 1, wherein the liquid collector and the guide tube are integrated, or wherein the liquid collector and the guide tube are fixedly connected in a splitting manner; and the liquid collector is allowed to be used separately from the guide tube.

4. The portable liquid collection device of claim 1, wherein the tube cover body has a hollow cylindrical structure or a hollow elliptical structure; the top of the tube cover body is provided with a tube plug; the tube cover body and the tube plug are integrated, or the tube cover body and the tube plug are fixedly connected in a splitting manner; one or more tube cover channels are disposed between an inner wall at the bottom of the tube cover body and the placing slot; one or more annular grooves are disposed between the inner wall at the top of the tube cover body and the placing slot; one or more transverse grooves are disposed on a surface at the top of the tube cover body; one or more elongated grooves are disposed from a surface of the inner wall at the top of the tube cover body to a surface of the one or more annular grooves; and the one or more annular grooves, the one or more transverse grooves and the one or more elongated grooves connect to each other.

5. The portable liquid collection device of claim 1, wherein the upper plug body and the middle plug body of the blocking plug are tightly combined with the tube cover body, and the diameter of the lower plug body of the blocking plug is matched with an inner diameter of a tube port of the collection tube body; the blocking plug forms a one-layer or dual-layer hollow annular structure; and the blocking plug is a rubber plug.

6. A method of using the portable liquid collection device of claim 1, wherein when the liquid collector, the guide tube and the liquid collection tube are used in combination, the needle-shaped structure of the guide tube penetrates the blocking plug of the collection tube cover to enter the collection tube body; after the inner-outer embedding connection structure formed between the inner wall at the top of the tube cover body and the outer annular structure of the guide tube is completed, a liquid and an air are in a flowing state; in the flowing state, the liquid first flows into the liquid collector, and then the liquid flows into the liquid collection tube via the guide tube, and the air in the liquid collection tube flows out of the liquid collection tube via the guide tube.

7. The method of claim 6, wherein the flowing state comprises a liquid flowing state and an air flowing state;
 the liquid flowing state comprises a first state, wherein in the first state, the liquid flows into the first flowing liquid hole of the liquid collector, then the liquid flows out of the at least one of the second flowing liquid holes of the guide tube via the liquid channel, and finally the liquid flows into the liquid collection tube; and
 the air flowing state comprises a second state, wherein in the second state, the air in the liquid collection tube flows into the at least one of the flowing gas holes of the guide tube, then the air flows out of the at least one of the flowing gas holes of the guide tube via the gas channel, and finally the air flows into an ambient.

8. The method of claim 7, wherein in the air flowing state, the air in the liquid collection tube flows out of the at least one of the flowing gas holes and then the air directly flows into the ambient; alternatively, in the air flowing state, the air in the liquid collection tube flows out of the at least one of the flowing gas holes, and then the air flows into the ambient via an air flowing path.

9. A portable liquid collection device, comprising a liquid collector, a guide tube and a liquid collection tube; wherein
 the liquid collector is shaped as a circular opening, and comprises at least a first flowing liquid hole and a first anti-slip structure;
 the guide tube comprises two ends, wherein a first end of the two ends of the guide tube connects to the liquid collector, a second end of the two ends of the guide tube is in a needle-shaped structure, and the second end of the two ends of the guide tube connects to the liquid collection tube; the guide tube is provided with an outer annular structure; the guide tube is provided with a plurality of second flowing liquid holes and a plurality of flowing gas holes; at least a liquid channel and at least a gas channel are disposed in a tube body of the guide tube; the at least a liquid channel connects to at least one of the second flowing liquid holes, wherein at least one of the second flowing liquid holes of the guide tube connects to the first flowing liquid hole of the liquid collector; the gas channel connects to at least one of the flowing gas holes; and
 the liquid collection tube comprises a collection tube body and a collection tube cover; the collection tube body and the collection tube cover are structurally connected through a connection manner; a surface of the collection tube body is provided with scale lines; the collection tube cover comprises a tube cover body and a blocking plug; an inner-outer embedding connection structure is formed between an inner wall at a top of the tube cover body and the outer annular structure of the guide tube; a placing slot for placing the blocking plug is disposed between the top of the tube cover body and a bottom of the tube cover body; a diameter of an inner wall at a top of the placing slot is smaller than a diameter of an inner wall at a bottom of the placing slot; a structure of the blocking plug is a three-layer structure, wherein a diameter of an upper plug body is smaller than a diameter of a lower plug body, and the diameter of the upper plug body and the diameter of the lower plug body are smaller than a diameter of a middle plug body; wherein the diameter of the upper plug body forms a left annular structure and the diameter of the lower plug body forms a right annular structure; wherein each of the left annular structure and the right annular structure is an arc structure; the placing slot is matched with the diameter of the middle plug body of the blocking plug; and the inner-outer embedding connection structure is also formed between the blocking plug and an inner wall of the tube cover body; and
 the collection tube body and the collection tube cover are structurally connected in the connection manner; the collection tube body is provided with a first connection structure, and the collection tube cover is provided with a second connection structure corresponding to the first connection structure; the connection manner comprises a thread connection manner, a snap-fit connection manner or a turning fastening connection manner; the collection tube body and the collection tube cover are provided with a second anti-slip structure; the second anti-slip structure is a dot structure, and the dot structure forms Braille.

10. The portable liquid collection device of claim 9, wherein the liquid collector comprises a concave surface that is a mesh structure or a first dot structure; and the first anti-slip structure is a second dot structure, and the second dot structure forms Braille.

11. The portable liquid collection device of claim 9, wherein the liquid collector and the guide tube are integrated, or wherein the liquid collector and the guide tube are fixedly connected in a splitting manner; and the liquid collector is allowed to be used separately from the guide tube.

12. The portable liquid collection device of claim 9, wherein the tube cover body has a hollow cylindrical structure or a hollow elliptical structure; the top of the tube cover body is provided with a tube plug; the tube cover body and the tube plug are integrated, or the tube cover body and the tube plug are fixedly connected in a splitting manner; one or more tube cover channels are disposed between an inner wall at the bottom of the tube cover body and the placing slot; one or more annular grooves are disposed between the inner wall at the top of the tube cover body and the placing slot; one or more transverse grooves are disposed on a surface at the top of the tube cover body; one or more elongated grooves are disposed from a surface of the inner wall at the top of the tube cover body to a surface of the one or more annular grooves; and the one or more annular grooves, the one or more transverse grooves and the one or more elongated grooves connect to each other.

13. The portable liquid collection device of claim 9, wherein the upper plug body and the middle plug body of the blocking plug are tightly combined with the tube cover body, and the diameter of the lower plug body of the blocking plug is matched with an inner diameter of a tube port of the collection tube body; the blocking plug forms a one-layer or dual-layer hollow annular structure; and the blocking plug is a rubber plug.

14. A method of using the portable liquid collection device of claim 9, wherein when the liquid collector, the guide tube and the liquid collection tube are used in combination, the needle-shaped structure of the guide tube penetrates the blocking plug of the collection tube cover to enter the collection tube body; after the inner-outer embedding connection structure formed between the inner wall at the top of the tube cover body and the outer annular structure of the guide tube is completed, a liquid and an air are in a flowing state; in the flowing state, the liquid first flows into the liquid collector, and then the liquid flows into the liquid collection tube via the guide tube, and the air in the liquid collection tube flows out of the liquid collection tube via the guide tube.

15. The method of claim 14, wherein the flowing state comprises a liquid flowing state and an air flowing state;
the liquid flowing state comprises a first state, wherein in the first state, the liquid flows into the first flowing liquid hole of the liquid collector, then the liquid flows out of the at least one of the second flowing liquid holes of the guide tube via the liquid channel, and finally the liquid flows into the liquid collection tube; and
the air flowing state comprises a second state, wherein in the second state, the air in the liquid collection tube flows into the at least one of the flowing gas holes of the guide tube, then the air flows out of the at least one of the flowing gas holes of the guide tube via the gas channel, and finally the air flows into an ambient.

16. The method of claim 15, wherein in the air flowing state, the air in the liquid collection tube flows out of the at least one of the flowing gas holes and then the air directly flows into the ambient; alternatively, in the air flowing state, the air in the liquid collection tube flows out of the at least one of the flowing gas holes, and then the air flows into the ambient via an air flowing path.

* * * * *